(12) United States Patent
Woehr

(10) Patent No.: US 7,186,239 B2
(45) Date of Patent: *Mar. 6, 2007

(54) SHORT CATHETER

(75) Inventor: Kevin Woehr, Felsberg (DE)

(73) Assignee: B. Braun Melsungen AG, Melsungen (DE)

( * ) Notice: Subject to any disclaimer, the term of this patent is extended or adjusted under 35 U.S.C. 154(b) by 335 days.

This patent is subject to a terminal disclaimer.

(21) Appl. No.: 10/779,370

(22) Filed: Feb. 13, 2004

(65) Prior Publication Data
US 2004/0162522 A1 Aug. 19, 2004

Related U.S. Application Data

(63) Continuation of application No. 09/727,747, filed on Dec. 1, 2000, now Pat. No. 6,709,419.

(30) Foreign Application Priority Data
Dec. 1, 1999 (DE) .......................... 299 21 084 U

(51) Int. Cl.
A61M 5/178 (2006.01)

(52) U.S. Cl. ................. 604/164.07; 604/110; 604/198; 604/164.08

(58) Field of Classification Search ................ 604/192, 604/198, 171, 110, 263, 164, 243
See application file for complete search history.

(56) References Cited

U.S. PATENT DOCUMENTS

| 4,250,881 A | 2/1981 | Smith |
| 4,790,828 A | 12/1988 | Dombrowski et al. |
| 4,929,241 A | 5/1990 | Kulli |
| 4,944,725 A | 7/1990 | McDonald |
| 4,952,207 A | 8/1990 | Lemieux |
| 4,978,344 A | 12/1990 | Dombrowski et al. |
| 4,994,041 A | 2/1991 | Dombrowski et al. |
| 5,049,136 A | 9/1991 | Johnson |

(Continued)

FOREIGN PATENT DOCUMENTS

EP 1 106 199 B1 6/2001

(Continued)

OTHER PUBLICATIONS

Office Action dated Jul. 28, 2005, Application No. 10/468,923, filed Feb. 2, 2004, (22 pages).

(Continued)

Primary Examiner—Nicholas Lucchesi
Assistant Examiner—Theodore J. Stigell
(74) Attorney, Agent, or Firm—Christie, Parker & Hale, LLP

(57) ABSTRACT

A catheter assembly is provided which provides a flexible catheter tube having one end provided with a catheter hub. A hollow needle having a needle hub on its end is installed in the catheter tube with its sharp end extending out from one end of the catheter tube and a portion of the needle extending through the catheter hub. A needle shield, which is on the needle within the interior of the catheter hub, is biased axially within the catheter hub with its ends being fixed to prevent axial expansion.

30 Claims, 2 Drawing Sheets

U.S. PATENT DOCUMENTS

| | | |
|---|---|---|
| 5,053,017 A | 10/1991 | Chamuel |
| 5,053,107 A | 10/1991 | Barber, Jr. |
| 5,120,320 A | 6/1992 | Fayngold |
| 5,135,504 A | 8/1992 | McLees |
| 5,215,525 A | 6/1993 | Sturman |
| 5,215,528 A | 6/1993 | Purdy et al. |
| 5,217,438 A | 6/1993 | Davis et al. |
| RE34,416 E | 10/1993 | Lemieux |
| 5,279,570 A | 1/1994 | Dombrowski et al. |
| 5,279,591 A | 1/1994 | Simon |
| 5,300,045 A | 4/1994 | Plassche, Jr. |
| 5,312,371 A | 5/1994 | Dombrowski et al. |
| 5,322,517 A | 6/1994 | Sircom et al. |
| 5,328,482 A | 7/1994 | Sircom et al. |
| 5,344,408 A | 9/1994 | Partika |
| 5,348,544 A | 9/1994 | Sweeney et al. |
| 5,419,766 A | 5/1995 | Chang et al. |
| 5,423,766 A | 6/1995 | Di Cesare |
| 5,458,658 A | 10/1995 | Sircom |
| 5,558,651 A | 9/1996 | Crawford et al. |
| 5,599,310 A | 2/1997 | Bogert |
| 5,611,781 A | 3/1997 | Sircom et al. |
| 5,662,610 A | 9/1997 | Sircom |
| 5,697,907 A | 12/1997 | Gaba |
| 5,843,048 A | 12/1998 | Gross |
| 5,882,337 A | 3/1999 | Bogert et al. |
| 6,004,294 A | 12/1999 | Brimhall et al. |
| 6,117,108 A * | 9/2000 | Woehr et al. .......... 604/110 |
| 6,224,569 B1 | 5/2001 | Brimhall |
| 6,280,419 B1 * | 8/2001 | Vojtasek .............. 604/192 |
| 6,287,278 B1 | 9/2001 | Woehr et al. |
| 6,443,929 B1 | 9/2002 | Kuracina et al. |
| 6,595,955 B2 | 7/2003 | Ferguson et al. |
| 6,616,630 B1 | 9/2003 | Woehr et al. |
| 6,749,588 B1 | 6/2004 | Howell et al. |

FOREIGN PATENT DOCUMENTS

| | | |
|---|---|---|
| WO | WO 97/42989 | 11/1997 |
| WO | WO 99/08742 | 2/1999 |
| WO | WO99/08742 | 2/1999 |
| WO | WO 00/69501 | 11/2000 |

OTHER PUBLICATIONS

Notice of Opposition to European Patent Office dated Apr. 26, 2006 regarding Patent No. 1,106,199; Application No. 00 124 007.6, Opponents Ref. No. EPE-98 348 (19 pages) with Supporting Publications D1-D5: (D1) WO 99/08742 (Publ. Date Feb. 25, 1999), (D2) WO 96/22800 (Publ. Date Aug. 1, 1996), (D3) EP 0 750 915 A2 (Publ. Date Jan. 2, 1997), (D4) US-B 5,662,610 (Publ. Date Sep. 2, 1997) and (D5) US-B 5,322,517 (Publ. Date Jun. 21, 1994).

Woehr, K., U.S. Appl. No. 11/327,206, filed Jan. 6, 2006 entitled "A Short Catheter", which is related to U.S. Appl. No. 10/779,370, filed Feb. 13, 2004 (11 pages).

\* cited by examiner

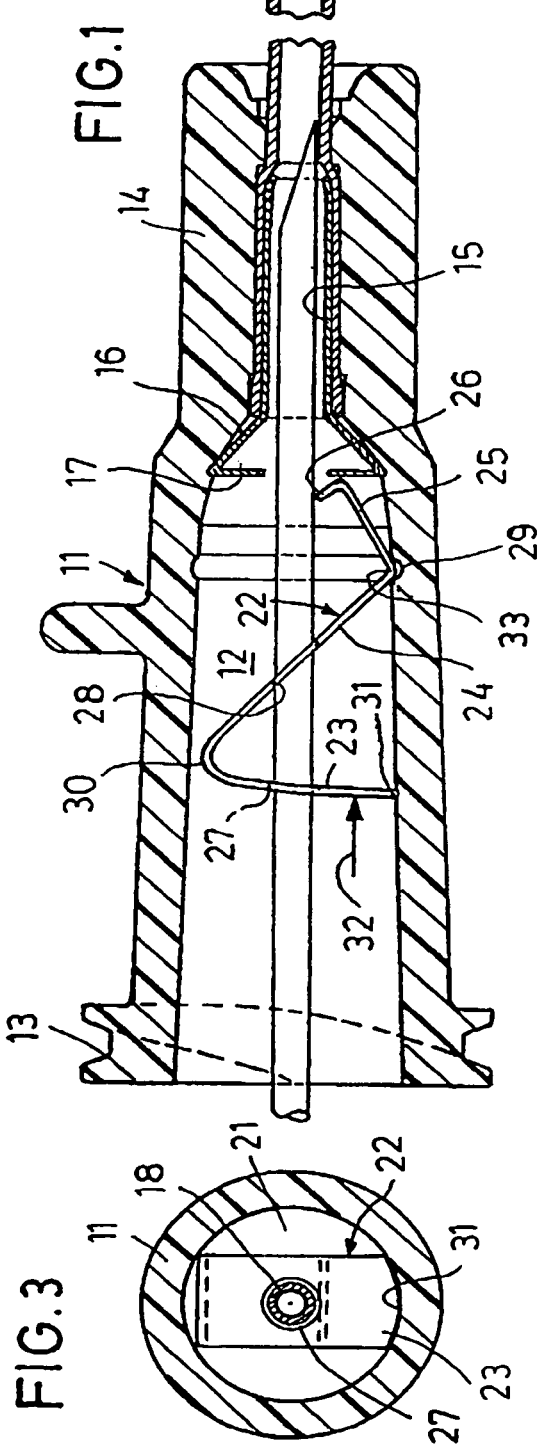
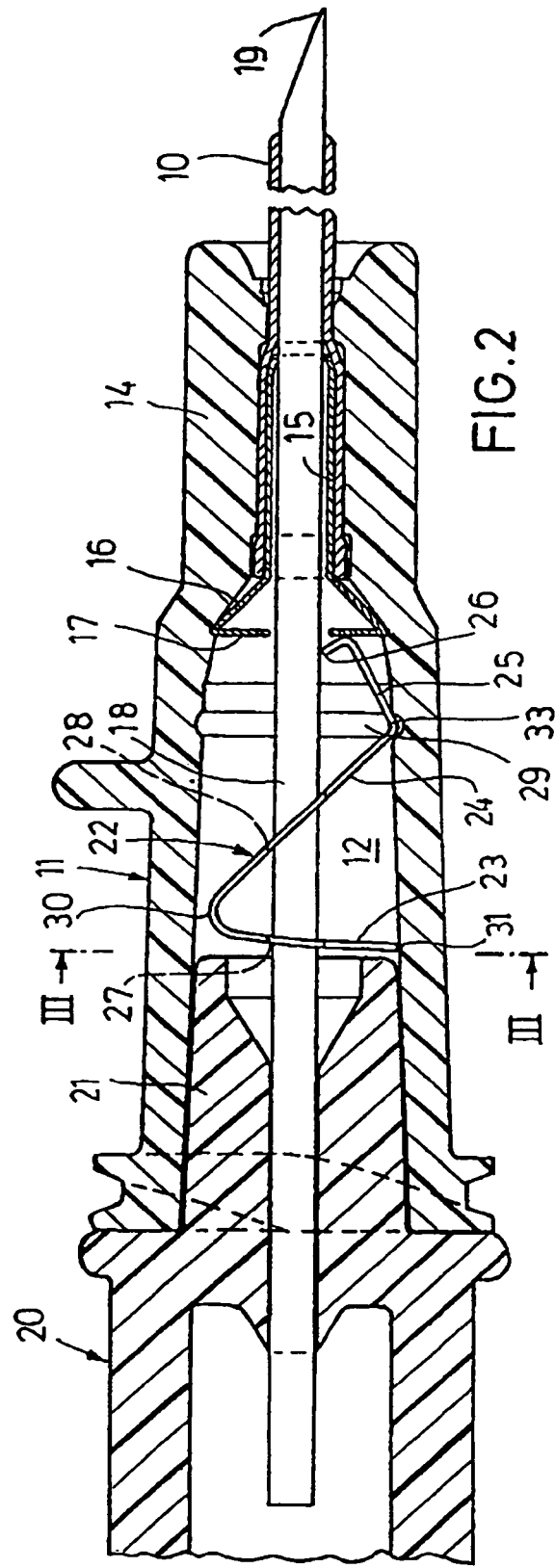

SHORT CATHETER

CROSS-REFERENCE TO RELATED APPLICATIONS

The present application is a continuation of application Ser. No. 09/727,747, filed on Dec. 1, 2000 now U.S. Pat. No. 6,709,419, entitled "A SHORT CATHETER," which claims priority to German Utility Model DE 29921084.7, filed on Dec. 1, 1999, the contents of which are expressly incorporated herein by reference.

BACKGROUND

The present invention refers to a short catheter in which the needle inserted into the catheter tube is made unserviceable by a needle shield after withdrawal.

Short catheters are also referred to as vein catheters or IV-catheters. They have a flexible catheter tube having one end provided with a catheter hub. A hollow needle is inserted into the catheter tube, the needle having a cutting needle tip at the distal end and a needle hub at the proximal end. By the needle tip, the needle and the surrounding catheter tube is inserted into the body of a patient. When the needle tip has entered a vein, the needle is withdrawn.

From WO 99/08742, a short catheter is known, wherein the needle is provided with a needle shield. The needle shield consists of a elastic metal clamp that is contained in the cavity of the catheter hub and has holes for the passage of the needle. A hook member of the needle shield presses the needle from the side. When, upon the withdrawal of the needle, the needle tip passes the hook member, the hook member snaps over the needle tip so that the hook member covers the needle tip which is no longer accessible. Thus, people are kept safe from being injured by the needle tip. In particular, the danger of contamination by germs clinging to the needle, transferred when the needle was used for the first time, is reduced. The needle shield guarantees that the needle can be used only once so that a contaminated needle cannot be used with another patient. To prevent the needle shield from slipping beyond the distal needle end, the needle may be provided with a corresponding locking means in the form of a notch or a not circular portion forming a distal stop for limiting the movement of the needle shield.

It is an object of the present invention to provide a short catheter comprising a needle shield wherein a clamping effect firmly holds the needle shield in the needle tip covering position.

The present short catheter has the features mentioned in claim 1. According to the invention, the needle shield is biased axially within the needle shield, its ends being fixed to prevent axial expansion In the biased state, the needle may easily be pushed through the holes in the needle shield since the holes are orientated such that the needle is easily displaced. In the activated state, i.e., when the needle tip has passed the hook member, the hook member snaps over the needle tip, thus releasing the axial bias of the spring element. The spring element is thereby returned to its stretched original shape. Thus, the holes that previously surrounded the needle with a slight gap suddenly become narrower in one direction, whereby the spring element firmly engages the needle. The release of the axial tension and the return of the spring element cause a tight clamping of the needle at the edges of the holes in the spring element. Therefore, in many cases, locking or blocking means at the needle can be omitted so that the needle must not be modified with respect to conventional needles.

To be able to accommodate the axially compressed needle shield in the interior of the catheter hub, the catheter hub must be provided with a holding means forming a stop for the distal end of the needle shield, i.e. the hook member. Preferably, such a holding means is a metal member protruding into the catheter tube and supporting the same in the catheter hub. Such a metal member is usually provided in a catheter hub as an internal catheter support. The metal member may be modified in a simple manner to -form an abutment shoulder for the needle shield. This abutment shoulder may be an end wall that is formed to the opening end of a funnel of the metal member.

Preferably, a proximal holding means consists of an end edge of the needle shield that projects into the wall of the catheter hub. This end edge may be sharpened and penetrate into the wall of the catheter hub, when the needle shield is mounted.

BRIEF DESCRIPTION OF THE DRAWINGS

The following is a detailed description of an embodiment of the invention with reference to the drawings, in which FIG. 1 is a longitudinal section through the short catheter, FIG. 2 is a longitudinal section after insertion of the needle into the short catheter being ready for use, FIG. 3 is a sectional view along line III—III in FIG. 2.

DETAILED DESCRIPTION

Figure 4:
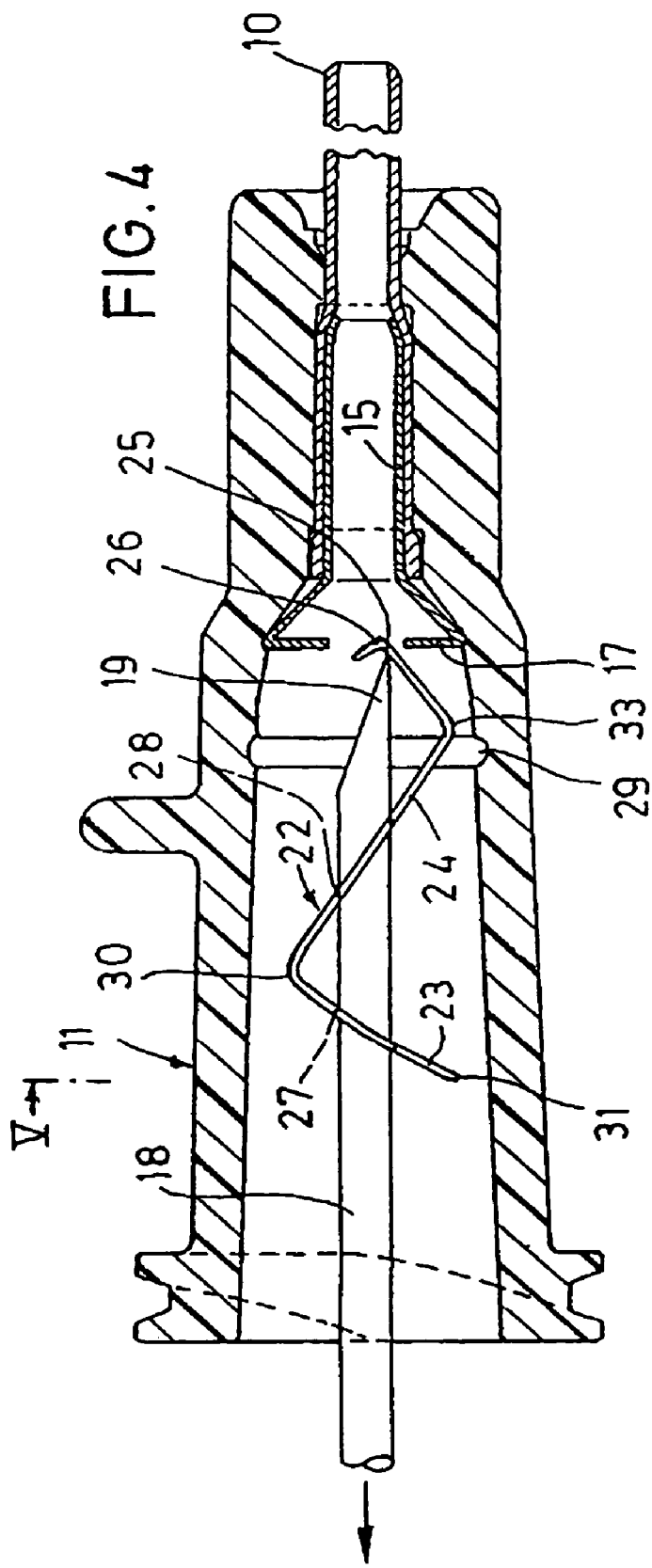
FIG. 4 is a longitudinal section during withdrawal of the needle.

The short catheter illustrated comprises a flexible catheter tube 10 of elastic plastic material having its proximal end provided with a catheter hub 11. The catheter hub 11 consists of an elongate hollow plastic member with a slightly conical interior 12 and a Luer connector 13 at the proximal end. The distal end portion 14 is tubular. The catheter tube 10 extends therethrough up to the interior 12. A tubular metal member 15 is inserted into the proximal end of the catheter tube 10, which expands the catheter tube and presses it against the wall of the tubular portion 14. At the proximal opening end of the metal member 15, the metal member is flared in the manner of a funnel 16. The opening end of the funnel 16 is formed with an end wall 17 directed radially inward.

A hollow needle 18 is inserted into the catheter tube 10, having a cutting needle tip 19 at the distal end. The needle 18 is made of steel. At the rear end, it is connected to a needle hub 20 of plastic material. The needle hub 20 abuts the proximal end of the catheter hub 11 and a frustoconical projection 21 thereof, loosely fitting into the catheter hub 11, protrudes into the interior 12.

The interior 12 accommodates the needle shield 22 consisting of a spring member made of bent spring steel sheet. The needle shield is generally bent in a Z-shape, with a rear leg 23, a middle leg 24 and a front leg 25 being provided in succession. The front leg 25 has a hook member 26 formed thereto, angled off by more than 90 degree. The rear leg 23 and the middle leg 24 are each provided with a hole 27, 28.

As illustrated in FIG. 1, the needle shield 22 is inserted into the catheter hub 11 while sitting on the needle 18, the hook member 26 being set against the end wall 17 of the metal member 16. Then, using a tool (not illustrated) inserted into the interior 12 from the proximal end, an axial pressure is exerted in the direction of the arrow 32, the needle shield 22 being compressed in the axial direction. The axial direction follows the orientation of the axis of the catheter tube 10.

During the axial compression, a front bend 33 of the needle shield, formed between the sections 24 and 25, is pressed into an inner circumferential groove 29 of the interior. An opposite bend 30 connects the sections 23 and 24.

In this compressed state of the needle shield 22, the holes 27, 28 are circular in axial projection. This means that the hole 28 in the oblique middle leg 24 is oval and is larger in the longitudinal direction than in the transverse direction.

When the needle shield 22 is compressed axially, the end edge 31 of the section 23 is pressed into the wall of the catheter hub 11. Thus, the rear end of the needle shield penetrates into the wall, whereas the front end of the needle shield is supported on the end wall 17. In this state, the needle 18 may be inserted from the proximal end, passing through the holes 27 and 28 with a clearance and being advanced without any problems. The hook member 26 is displaced radially outward by the needle 18 so that, after further advancing the needle 18, it presses against the needle from the side.

Figure 5:
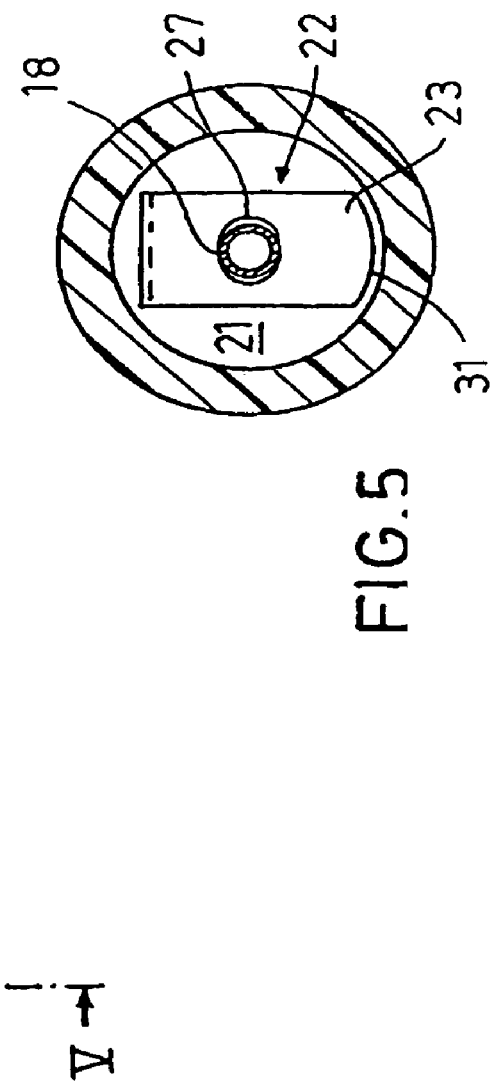
FIG. 5 is a sectional view along line V—V of FIG. 4.

FIGS. 4 and 5 illustrate the short catheter during the withdrawal of the needle 18 from the catheter tub 10 and the catheter hub 11. During the withdrawal of the needle 18, the hook member 26 that previously pressed against the needle from the side snaps over the needle tip 19. The previously axially compressed needle shield is relaxed and the end edge 31 comes clear of its engagement in the needle hub. The resilient needle shield 22 thus extends axially and the sharp edges of the holes 27, 28 firmly engage the needle 18. As can be seen in FIG. 5, the hole 27 becomes an ellipse, seen in axial projection. As soon as the needle shield has been activated by the needle tip 19 passing the hook member 26, the hook member 26 snaps over the needle tip and the needle shield firmly engages the needle. The hook member 26 now covers the needle tip and blocks any distal movement of the needle tip relative to the needle shield. The fact that the needle shield is axially expanded and separates from the catheter hub at its end edge 31 makes it freely movable within the catheter hub. After the needle shield is activated, its two holes 27, 28 engage a total of four points on the needle, as shown in FIG. 5. The needle 18 is a cylindrical round needle without any notches, projections or non-circular portions.

What is claimed is:

1. A catheter assembly comprising:
   a needle hub comprising a proximal end, a distal end, an exterior surface and an interior surface defining an interior cavity;
   a needle attached to the distal end of the needle hub comprising a needle tip and a needle axis;
   a catheter hub comprising a proximal end, a distal end an exterior surface and an interior surface defining an interior cavity;
   a catheter tube comprising a lumen attached to the distal end of the catheter hub;
   a protective clip comprising a resilient arm and a proximal wall comprising an opening sized to accommodate the needle, the opening comprising a perimeter comprising a first perimeter portion and a second perimeter portion;
   a ready to use position in which the catheter hub is removeably engaged to a nose section of the distal end of the needle hub and the needle projected into the lumen of the catheter tube and defining a holding space bounded by the interior cavity of the catheter hub and a portion of the nose section of the needle hub; the protective clip being positioned in the holding space with a portion associated with the resilient arm of the protective clip contacting an engagement surface on the interior cavity of the catheter hub;
   a retracted position in which the catheter hub is disengaged from the nose section of the needle hub, the portion associated with the resilient arm of the protective clip no longer contacting the engagement surface on the interior cavity of the catheter hub, and the proximal wall of the protective clip positioned at an angle to the axis of the needle such that the needle contacts the first perimeter portion and the second perimeter portion of the perimeter to fix relative movement between the needle and the tip protector.

2. The catheter assembly of claim 1, wherein the resilient arm is integrally formed with the proximal wall.

3. The catheter assembly of claim 1, wherein the protective clip further comprises a second resilient arm comprising an opening.

4. The catheter assembly of claim 3, wherein the second resilient arm extends from the proximal wall and the resilient arm extends from the second resilient arm.

5. The catheter assembly of claim 4, wherein the resilient arm comprises a hook member.

6. The catheter assembly of claim 5, wherein the hook member abuts the needle.

7. The catheter assembly of claim 3, wherein the opening of the second resilient arm comprises a perimeter comprising a first perimeter portion and a second perimeter portion.

8. The catheter assembly of claim 7, wherein the needle contacts the first perimeter portion and the second perimeter portion of the perimeter of the second resilient arm.

9. The catheter assembly of claim 1, further comprising a metallic tubular member coaxially disposed with the catheter tube.

10. The catheter assembly of claim 1, wherein the needle comprises a single generally uniform diameter.

11. The catheter assembly of claim 1, wherein the catheter hub comprises a Luer connector.

12. The catheter assembly of claim 1, wherein the proximal wall comprises a end edge abutting the interior surface of the interior cavity of the catheter hub.

13. A catheter assembly comprising a needle hub having an exterior surface and a needle having a needle tip attached thereto removeably engaged to a first portion of an interior cavity of a catheter hub comprising a catheter rube extending distally from the catheter hub with the needle extending through the catheter tube and the needle tip extending beyond the catheter tube;
   a needle protective clip comprising a proximal wall having an opening and a resilient portion positioned in the interior cavity of the catheter hub having the needle passing through the opening and the resilient portion biased by the needle, the opening comprising a perimeter comprising a first perimeter portion and a second perimeter portion;
   wherein a second portion of the interior cavity of the catheter hub is removeably engaged to a portion of the needle protective clip such that the needle protective clip is retained within the cavity of the catheter hub by the engagement when the needle is retracted from the catheter tube by moving the needle hub proximally relative to the catheter hub; and
   wherein the needle protective clip is separable from the catheter hub when the needle tip enters the interior cavity of the catheter hub and the resilient portion of the needle protective clip is unbiased by the needle; whereupon further withdrawing of the needle further separates the second portion of the interior cavity of the catheter hub from the portion of the needle protective clip and the needle contacts the first perimeter portion and the second perimeter portion of the perimeter to fix relative movement between the needle and the tip protector.

14. The catheter assembly of claim 13, wherein the resilient portion is integrally formed with the proximal wall.

15. The catheter assembly of claim 13, wherein the resilient portion comprises a hook portion abutting the needle.

16. The catheter assembly of claim 13, wherein the protective clip further comprises a second resilient portion comprising an opening.

17. The catheter assembly of claim 16, wherein the second resilient portion extends from the proximal wall and the resilient portion extends from the second resilient portion.

18. The catheter assembly of claim 17, wherein the opening of the second resilient portion comprises a perimeter comprising a first perimeter portion and a second perimeter portion.

19. The catheter assembly of claim 18, wherein the needle contacts the first perimeter portion and the second perimeter portion of the perimeter of the second resilient portion.

20. The catheter assembly of claim 13, wherein the catheter hub comprises a Luer lock.

21. The catheter assembly of claim 13, wherein the needle hub further comprises a nose portion and wherein the needle attaches to the nose portion of the needle hub.

22. The catheter assembly of claim 21, wherein the nose portion comprises an exterior surface mid wherein the interior cavity of the catheter hub is in contact with the exterior surface of the nose portion.

23. The catheter assembly of claim 13, wherein the needle hub comprises an interior surface defining an interior cavity.

24. The catheter assembly of claim 23, wherein a proximal end of the needle extends into the interior cavity of the needle hub.

25. The catheter assembly of claim 13, wherein the second portion of the interior cavity of the catheter hub engaged to the needle clip comprises a groove.

26. The catheter assembly of claim 25, wherein the groove is an annular groove.

27. A catheter assembly comprising a catheter hub having a catheter tube extending from a distal end thereof, the catheter tube comprising a lumen and a distal end and the catheter hub comprising an interior cavity comprising an interior surface having a clip engagement wall surface formed thereon;

a needle hub having a needle attached to a distal end thereof comprising a needle tip;

a ready position in which the needle extends through the lumen of the catheter tube and the needle tip extends beyond the distal end thereof;

a retracted position in which the needle moves proximally relative to the catheter hub and the needle tip is at a position within the interior cavity of the catheter hub;

a needle protective clip comprising a proximal wall having an opening, a resilient member comprising a needle distally blocking member, and an engagement segment for retaining the needle protective clip to the catheter hub during movement of the needle between the ready position and the retracted position, the opening comprising a perimeter comprising a first perimeter portion and a second perimeter portion;

wherein when the needle is in the ready position, the needle protective clip is positioned over the needle in the interior cavity of the catheter hub and the needle passes through the opening of the proximal wall; the resilient portion is biased by a side of the needle; and the engagement segment is engaged to the clip engagement wall surface of the interior surface of the catheter hub;

wherein when the needle moves from the ready position towards the retracted position, the clip engagement wall surface of the catheter hub and the engagement segment on the needle protective clip interact to prohibit relative movement between the catheter hub and the needle protective clip until the needle moves proximally of the needle distally blocking member whereupon the resilient member is no longer biased by the aide of the needle, the needle distally blocking member moves to block the needle tip, and, whereupon further needle movement, the needle protective clip separates from the catheter hub and the needle contacts the first perimeter portion and the second perimeter portion of the perimeter to fix relative movement between the needle and the tip protector.

28. The catheter assembly of claim 27, wherein the resilient member and the engagement segment of the protective clip are integrally formed with the proximal wall.

29. The catheter assembly of claim 27, wherein the clip engagement wall of the interior surface of the catheter hub comprises a groove.

30. The catheter assembly of claim 29, wherein the groove is annular.

* * * * *